United States Patent [19]

Nowacki et al.

[11] Patent Number: 5,197,476
[45] Date of Patent: Mar. 30, 1993

[54] LOCATING TARGET IN HUMAN BODY

[76] Inventors: Christopher Nowacki, 1552 Chickamauga, Long Grove, Ill. 60047; Mart T. Horbal, 2 S. 530 Iroquois Cts. West, Warrenville, Ill. 60555

[21] Appl. No.: 777,432

[22] Filed: Oct. 11, 1991

Related U.S. Application Data

[63] Continuation of Ser. No. 320,110, Mar. 16, 1989, abandoned.

[51] Int. Cl.$^5$ ............................................. A61B 17/22
[52] U.S. Cl. ........................ 128/660.03; 128/240 EL
[58] Field of Search ................. 128/24 AA, 916, 915, 128/660.01, 660.03, 24 EL

[56] References Cited

U.S. PATENT DOCUMENTS

| | | | |
|---|---|---|---|
| 4,620,546 | 11/1986 | Aida | 128/24 AK |
| 4,655,227 | 4/1987 | Gracovetsky | 128/781 |
| 4,664,130 | 5/1987 | Gracovetsky | 128/781 |
| 4,699,156 | 10/1987 | Gracovetsky | 128/781 |
| 4,722,340 | 2/1988 | Takayama | 128/24 AA |
| 4,757,820 | 7/1988 | Itoh | 128/24 AA |
| 4,763,652 | 8/1988 | Brisson | 128/24 AA |
| 4,821,729 | 4/1989 | Makofski | 128/660.03 |
| 4,896,673 | 1/1990 | Rose | 128/660.03 |

OTHER PUBLICATIONS

Sales brochure, Northern Digital Inc. of Waterloo, Canada, pp. 1-4, Jul. 1987.
Sales brochure, Spinex Medical Corporation of Montreal Canada, pp. 1-2, "The Spinoscope Pinpoints the location of Spinal dysfunction", undated.
Sales brochure, Spinex Medical Corporation of Montreal, Canada, pp. 1-6, "Spinoscope:Freedom of Movement during examination", undated.
Gracovetsky et al., "Non-Invasive Assessment of Spinal Function", pp. 1-10, article from Concordia Univ., Montreal, Canada, undated.
Rowell et al., "Human Movement Analysis", Soma Engineering for the Human Body, pp. 13-20, undated.
Ladin et al., "Segmental Analysis in Kinesiological Measurements", pp. 110-121, SPIE, vol. 1356 Image Based Motion Meas., 1990.

*Primary Examiner*—Lee S. Cohen
*Assistant Examiner*—K. M. Pfaffle
*Attorney, Agent, or Firm*—Robert M. Wolters

[57] ABSTRACT

Apparatus and methods for locating a target in a living body are provided. A three-dimensional frame carries a plurality of infrared light emitting diodes, and this frame is placed on a table. The infrared LEDs are strobed by a computer. The position of the infrared LEDs is monitored by a pair of infrared sensitive cameras and stored in a computer. The frame is then removed and a living body is placed within or closely adjacent to the volume. An ultrasonic probe is hand held within the volume and is provided with a plurality of infrared LEDs so that the probe can be monitored by the cameras. The positions of the probe LEDs are compared in the computer with the initial position of the frame LEDs so that the position of the probe can be determined quite accurately, and the position of the target in the body can be displayed on a computer monitor.

14 Claims, 2 Drawing Sheets

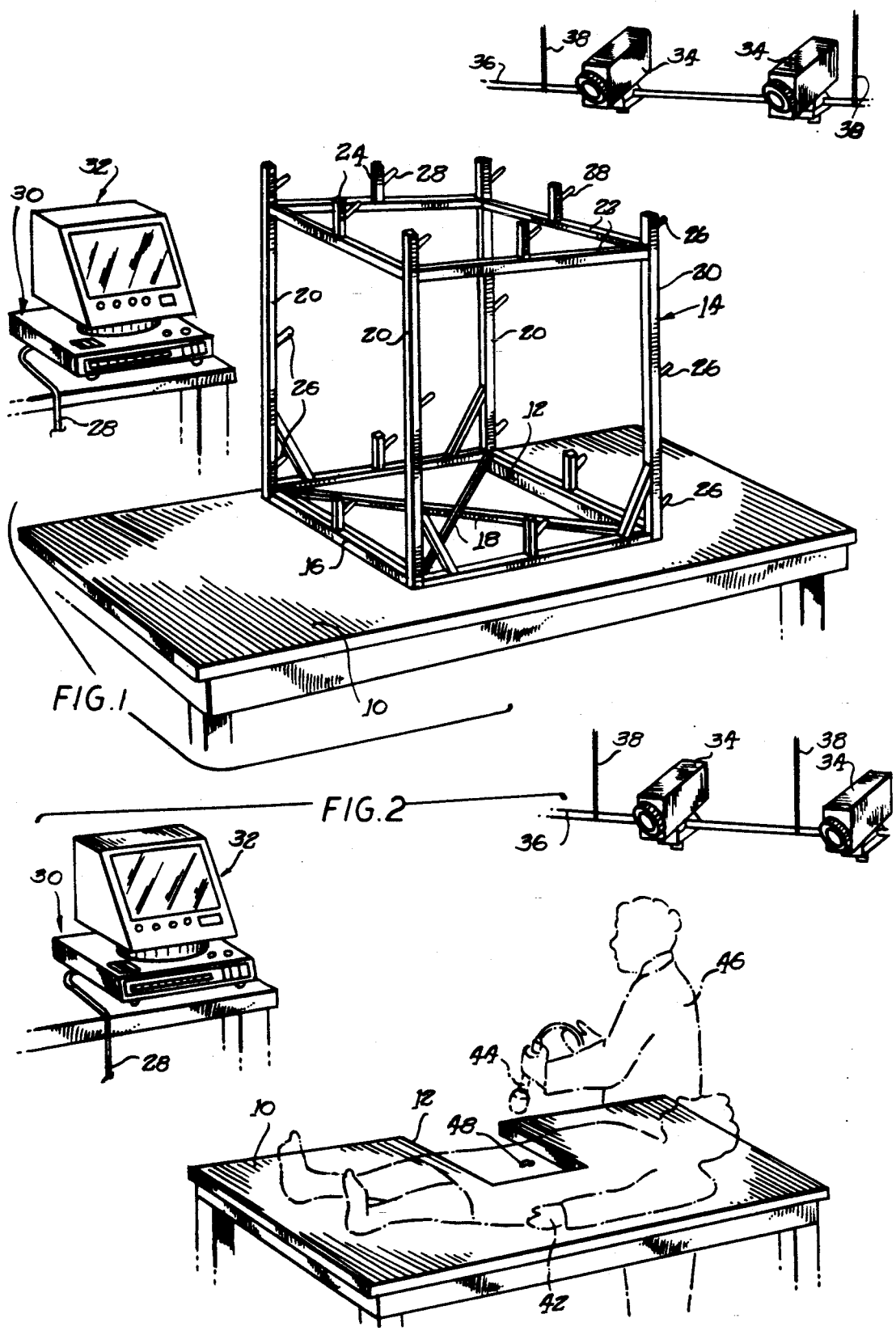

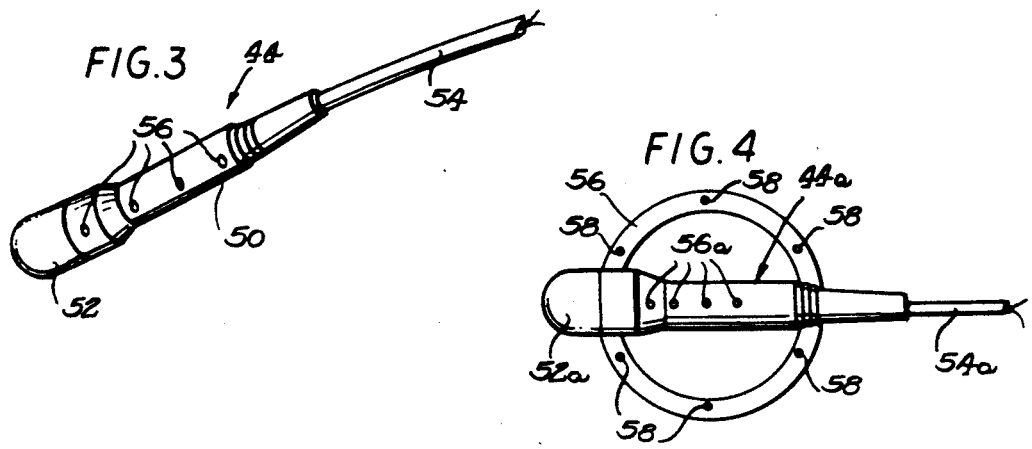
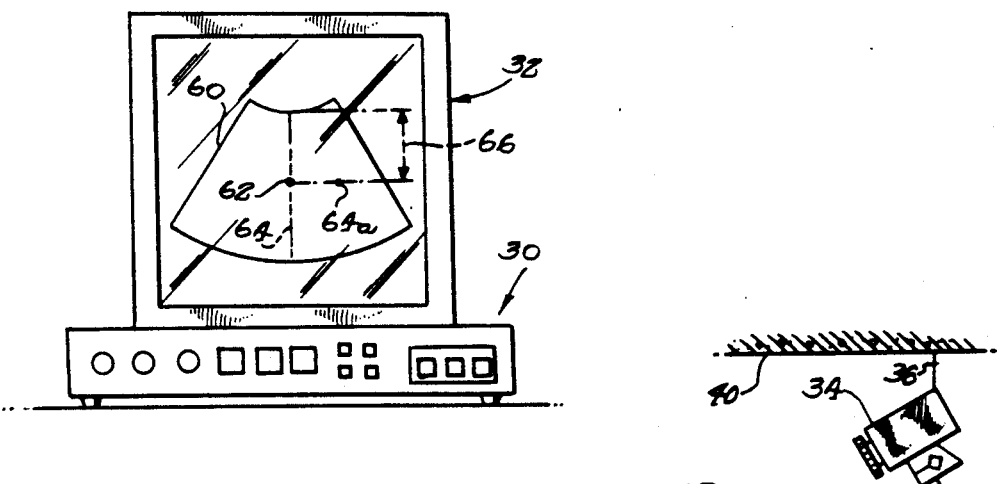
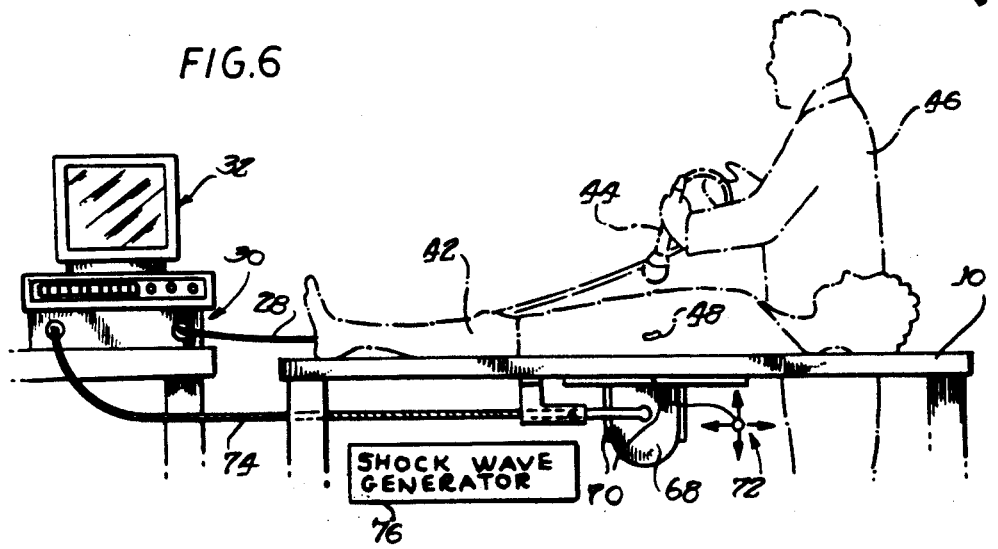

ent application Ser. No. 07/320,110, filed Mar. 6, 1989, now abandoned.

LOCATING TARGET IN HUMAN BODY

This application is a continuation of application Ser. No. 07/320,110, filed Mar. 6, 1989, now abandoned.

BACKGROUND OF THE INVENTION

Locating targets in the human body by ultrasound is a known procedure. In extracorporeal shockwave lithotripsy a concretion or kidney stone in a kidney, ureter, or bladder by means of ultrasound is known. It is the general procedure to use an articulated arm carrying an ultrasonic transducer that both sends out and receives the ultrasound signal. Devices are connected in the articulated arm to indicate the angles between various arm segments, and the angles thereof relative to a base. Movement of such articulated arms is necessarily restricted, and the arms themselves tend to get in the way.

OBJECTS AND SUMMARY OF THE PRESENT INVENTION

It is an object of the present invention to provide apparatus and methods for ultrasonic location of kidney stones and other targets in the human body, wherein an ultrasound transducer is hand held and freely movable within an operating area, and not restricted by connection to an articulated arm.

More particularly, it is an object of the present invention to provide means and methods for precisely locating in space an ultrasonic transducer which is hand held and freely movable without the constraints imposed by an articulated arm or the like.

In accordance with the present invention an examining table is provided on which a patient is to lie. Before the patient is so positioned a three-dimensional frame is placed on the table in the area where the target within the human body is to be detected. Infrared markers in the form of light emitting diodes (LEDs) are disposed at known locations on the frame. Two infrared cameras are disposed in a fixed location overseeing the area where the frame is disposed. Both the infrared light emitting sources on the frame and the cameras are connected to a computer. The use of two cameras provides a three-dimensional picture, and the light emitting diodes are sequentially strobed by the computer. The locations of the strobed LEDs are noted by the cameras and this information is stored in the computer.

Subsequently, the frame is removed, and a patient is placed on the examining table. A handholdable ultrasonic scanner is held in the hand above the patient, and is moved around. The ultrasound transducer is provided with light emitting diodes in the infrared region, and these are sequentially strobed. The positions of the LEDs on the transducer are noted by the cameras, and fed to the computer. An image on the computer monitor sets forth the precise position of the ultrasonic probe. The ultrasonic image is read by one skilled in that art, and when the target, be it a concretion, a tumor, etc. is located in the ultrasound scan, the precise position thereof can be determined by the computer from the position of the ultrasonic probe. This can be used solely for diagnostic purposes, or can be either connected through a computer or handled manually to a treating device, such as an extracorporal shockwave lithotripsy device.

THE DRAWINGS

The present invention will best be understood from a study of the following specification when taken in connection with the accompanying drawings wherein:

FIG. 1 is a perspective view showing equipment in accordance with the present invention as set up for locating the parameters of the target area;

FIG. 2 is a perspective view generally similar to FIG. 1, but with a patient in place rather than the set-up frame;

FIG. 3 is a perspective view of an ultrasonic scanner used in connection with the present invention;

FIG. 4 is a side view of a modified form of ultrasonic scanner;

FIG. 5 is a view showing the image seen on the monitor for the computer; and

FIG. 6 is a side view showing the location of a target in the human body in combination with apparatus for treating the target.

DETAIL DISCLOSURE OF THE ILLUSTRATED EMBODIMENTS

Attention should be directed first to FIG. 1 wherein there is seen an examining table 10. The table is provided with a cutout or relieved area 12 which may be used for treatment as well as for target detection. A three-dimensional frame 14 is positioned over opening 12 in the table and covering just slightly more space than the opening. If the table is to be used only for diagnostic purposes the opening is not required. The three-dimensional frame may vary somewhat in relative dimensions, but generally is in a shape approaching a cube, comprising four lower horizontal members 16 crossbraced by braces 18. Four uprights 20 at the corners of the horizontal members or base are braced near the top by horizontal members 22 in the form of a square or rectangle. The upright members extend above the horizontal members 22, and intermediate stub uprights 24 extend upwardly from the midsections of the horizontal members 22. Each of the upright members 20 has a plurality of infrared locators 26 thereon in vertically spaced relation, and including the upstanding portions above the horizontal members 22. In addition, each immediate upstanding member 24 is provided with a similar infrared locating member 28. Each of the infrared locators 26 includes a light emitting diode (LED) individually connected by means of a suitable cable, shown in part at 28, to a computer 30 having a monitor 32. The computer strobes the infrared locators 26 in predetermined sequence.

In addition to the foregoing, there are two infrared sensing cameras 34 mounted in spaced relation on a horizontal support 36 depending from vertical members 38 secured to a support such as a ceiling 40. The strobed LEDs are sensed by the cameras 34, thus providing a three-dimensional or stereo image, the information of which is connected to the computer by means such as the aforesaid cable 28. Information picked up by the cameras and transmitted to the computer is stored in the computer as to the location of each of the infrared devices 28, thereby establishing a three-dimensional volume or space for reference.

The frame 14 then is removed from the table, and a patient is placed in horizontal position on the table as indicated at 42. An ultrasonic strobe 44 is handheld by a doctor or technician 46. In the illustrated example the patient has a kidney stone 48, the location of which is to be determined. In this particular case where treatment may be combined with diagnosis the patient is positioned so that the kidney stone 48 lies above the cut-out or opening 12 in the table.

The probe 44 as best may be seen in FIG. 3, is of type generally known, having a handle portion 50 and an ultrasonic transducer 52 at the end thereof. The transducer is of a type that sweeps back and forth over a limited arcuate extent, but sending out a supersonic signal and receiving it as reflected. The probe is connected by means such as a cable 54 to the computer 30. The probe 44 departs from previously known probes in the provision of a plurality of infrared locators 56 spaced along its length. There locators again are conveiently infrared LEDs, and as the probe is manually moved about in rather free fashion within the space or volume previously determined by the infrared locators on the frame 14 the position of the probe is discerned by the cameras 34 and the three-dimensional information therefrom is transmitted to the computer which notes the position of the probe relative to the initial infrared locators 26 on the frame 14. The position of the probe thus is known including both the location and the angular disposition of the probe.

An improved form of probe is shown in FIG. 4. Most of the parts are the same as previously disclosed, and like parts are identified by similar numerals with the addition of the suffix a. In addition, a planar ring 56 is imposed on the probe and is provided with additional light emitting diode infrared locators 58. This provides additional information to the computer which allows rotational position of the probe to be entered as well as the position and angular disposition thereof.

The display on the computer monitor 32 is shown in FIG. 5, with a swept area indicated at 60 corresponding to the oscillation of the ultrasonic transducer. With the first form of the probe as shown in FIG. 3 it is necessary to move the probe about so that the target 62 lies on the axis 64 of the display. However, with the second form of the probe as in FIG. 4 the probe need not be moved to position the target on the axis, but it can be off axis as indicated at 64a. The angular position of the target relative to the probe is thus precisely located, the distance as indicated at 66 can be ascertained by means of a known caliper feature indicated by the double headed arrow 66.

As will be apparent, the probe is free to move in the space initially laid out by the frame 14, and its movement is not constrained by the usual articulated arm. It will be understood that the definition of the space or volume which is established by the frame 14 could otherwise be done by permanently fixed infrared LEDs. However, the frame allows a greater freedom of operation.

The present invention can be used not only in locating targets, but also in combination with treatment of targets. One such example is shown in FIG. 6. A water-filled ellipsoidal reflector comprising a part of a shockwave generator 68 is disposed beneath the opening or cut-out 12 in the table. The shockwave device or apparatus is mounted on suitable horizontal and vertical tracks 70 for movement thereof in either or both of two directions horizontally, and also up and down, and indicated by the arrow diagram 72 in FIG. 6. An electrical control cable 74 is connected to the ellipsoidal reflector and related apparatus including positioning motors therefore so that the computer 30 will control positioning of the ellipsoidal reflector relative to the kidney stone 48. An electrical shockwave generator 76 is connected electrically to the ellipsoidal reflector and related apparatus 68 to cause generation of a spark in the water in the reflector, with a resulting shockwave which is focused on the kidney stone in accordance with known techniques.

Manual holding and disposition of the probe has several advantages as contrasted with the previous mounting of the ultrasonic probe on an articulated arm. It is much easier to use, and the physician or technician need not drag a mechanical contraption around as in the prior art. The probe can be used to locate any sort of target, such as a tumor or growth in the uterus, in the lungs, or a concretion in the kidney, or some other target in other bodily tissues. Any target that a qualified technician can identify on the screen can be located. There is less maintenance that is necessary with the prior articulated arm. The diagnostician works an ultrasound tool with which he is familiar. The probe has a much greater reach or range of position than is possible with an articulated arm.

The present invention will now be well understood by those skilled in the art. The specific embodiments will be understood as being for illustrative purposes only. Persons skilled in the art will no doubt be able to envision variations thereof, and these will be understood as forming a part of the present invention insofar as they fall within the spirit and scope of the appended claims.

The invention is claimed as follows:

1. The method of locating an ultrasonic probe in order to locate a target in a living body which comprises disposing a plurality of first electrically operated radiation emitting devices about a reference volume, monitoring said devices with three-dimensional camera means sensitive to the radiation emitted by said devices, strobing said first radiation emitting devices with a computer to cause said devices to emit radiation sequentially, storing information from said camera means in said computer as to respective positions of said radiation emitting devices, removing said first radiation emitting devices from their disposition about said reference volume, placing a living body having the target therein at least in part in said reference volume and holding the ultrasonic probe substantially within said volume and scanning said living body ultrasonically with said probe, displaying the scanned portion of the body including the target on a display screen and observing the display, said probe having a second plurality of electrically operated radiation emitting devices thereon, strobing said second plurality of radiation emitting devices with said computer, and monitoring the second plurality of radiation emitting devices with said three-dimensional camera means to detect the position of said probe within said volume.

2. The method as set forth in claim 1 wherein said first and said second plurality of electrically operated radiation emitting devices comprise infrared light emitting devices, and said camera means is sensitive to the infrared light.

3. The method as set forth in claim 1 wherein said first plurality of radiation emitting devices are disposed on a rigid three-dimensional frame wherein the step of disposing said devices about the reference volume comprising locating said frame about said volume, wherein the step of removing said first radiation emitting devices before said living body is placed at least in part in said referenced volume comprises removing said frame.

4. The method as set forth in claim 3 which includes placing said frame on an examining table to dispose said first plurality of radiation emitting devices about said volume, the further step of removing said frame from said examining table, and subsequently placing said living body on said table.

5. The method as set forth in claim 1 and further including means for therapeutically, treating said target, and positioning said treating means in accordance with a target location as determined by said ultrasonic probe.

6. The method as set forth in claim 5 wherein the step of positioning the treating means comprises utilizing said computer to position said treating means.

7. Apparatus for locating an ultrasonic probe in order to locate a target in a living body comprising a first plurality of radiation emitting devices, means for supporting said first plurality of radiation emitting devices about a reference volume, three-dimensional camera means sensitive to the radiation emitted by said first plurality of radiation emitting devices, means for mounting said camera means in position to monitor said first plurality of radiation emitting devices, computer means for sequentially strobing said first plurality of radiation emitting devices, means interconnecting said computer means, said camera means and said first plurality of radiation emitting devices, table means for supporting the living body having a target therein at least in part in said volume, wherein said first radiation emitting devices are adapted to be removed from their disposition about said reference volume, an ultra sound probe, a second plurality of radiation emitting devices on said probe and of the same type as the first plurality of radiation emitting devices connected to said computer means, said probe being adapted to be supported manually substantially within said volume for ultrasonic scanning of the body including the target, said computer means for sequentially strobing said second plurality of radiation emitting devices to detect the position of said probe within said volume, and a display screen connected to said computer means for displaying an image related to said scanned body.

8. Apparatus as set forth in claim 7 wherein the means for supporting said first plurality of radiation emitting devices comprises a three-dimensional rigid frame placed on said table means and removed therefrom prior to placing a living body on said table.

9. Apparatus as set forth in claim 7 wherein said probe has an elongated body with some of said second plurality of radiation emitting devices thereon, and means for mounting others of said second plurality of radiation emitting devices outwardly of said probe body.

10. Apparatus as set forth in claim 7 wherein said first and second radiation emitting devices comprise infrared light emitting devices.

11. Apparatus as set forth in claim 7 and further including means for therapeutically treating said target, and means for positioning said treating means in accordance with a position of the target as determined by said ultrasonic probe.

12. Apparatus as set forth in claim 11 wherein the means for positioning said target treating means is interconnected with and controlled by said computer means.

13. Apparatus for locating an ultrasonic probe to locate a target in a human body comprising three dimensional camera means, means for supporting said camera means at an elevated location, a patient examining table and shock wave generating means being disposed within the aspect seen by said three dimensional camera means, means for moving said shock wave generating means being horizontally and vertically, the ultrasound probe and an ultrasound scan screen apparatus being interconnected with one another, a plurality of radiation sources carried by said probe, said three dimensional camera means for viewing said plurality of radiation sources, and computer means, said computer means, said ultrasound probe radiation sources, and said ultrasound scan screen apparatus being electrically interconnected, said computer means for strobing said probe radiation sources sequentially, said ultrasound scan screen apparatus having means for displaying X, Y and Z coordinates and angular positioning of said probe relative to said target to determine the positioning of said probe relative to said target and to determine the desirable amount, direction and elevation of movement of said shock wave generating means to position said target as located by said probe and said scan screen apparatus at a desired location.

14. Apparatus as set forth in claim 13 wherein said radiation sources comprise devices for emitting infrared light, and wherein said camera means is sensitive to said infrared light.

* * * * *